United States Patent [19]

McRae

[11] Patent Number: Plant 6,327

[45] Date of Patent: Oct. 11, 1988

[54] LILY PLANT NAMED 'POLKA DOT'

[75] Inventor: Edward A. McRae, Boring, Oreg.

[73] Assignee: Melridge, Inc., Aurora, Oreg.

[21] Appl. No.: 926,713

[22] Filed: Nov. 4, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant bearing large clusters of medium sized, upright flowers particularly characterized by their deep pink, copiously spotted, and cream-centered coloration, the flowers being of excellent form and long persistence. The plant is of tall stature with abundant, relatively short leaves and its ability to be forced into flower out of season makes it especially suitable as a cut flower variety. The color pattern and silhouette of this new plant are completely new in the upright Asiatic divisions of lilies suited to cut flower forcing and to mass commercial cultivation. The plant is highly resistant to disease and shows high tolerance of virus, making it an excellent garden plant; and the bulbs may be precooled and forced throughout the year for cut flower production. The clone is vigorous and a good grower and propagator.

1 Drawing Sheet

BACKGROUND OF THE NEW PLANT

This new variety of lily plant originated as a seedling selected from a group of seedlings planted by me at Sandy, Oreg., with seeds produced by using the clonal cultivar 'Peachblush' as the seed parent and as the pollen parent, a pink seedling selected from the cross of [('Enchantment'×an upright, pink Asiatic seedling)×-'Gypsy']; the object of this breeding effort being the production of lilies in shades of pink and peach well suited to forcing for cut flower production out of season, heretofore unknown in the lily breeding art.

This particular seedling was selected for propagation because of its deep pink, cream-throated coloration and copious spotting in the center only of the flower, a color pattern unique in this type of lily, and this selected seedling was asexually reproduced by me at Sandy, Oreg., with such satisfactory results that successive generations of this plant, produced by bulb scale propagation and by natural propagation from bulblets, have demonstrated that the novel and distinctive characteristics of this new plant hold true under asexual propagation from generation to generation and appear to be firmly fixed.

This new variety remains relatively tall and is not overly susceptible to bud abortion when forced into flower out of season as a cut flower plant; and in addition the clone possesses to a high degree the desirable characteristics of hybrid vigor, great hardiness, and disease resistance, as well as possessing all of the desired characteristics of excellence of form, color and habit. The clone is vigorous and a good grower and propagator, as observed at Sandy, Oreg.

This plant is well suited to forcing out of season when the bulbs are dug at the appropriate time and properly precooled; October-dug bulbs, properly precooled and potted in January, will flower under glass in western Oregon, with no supplemental lighting and at moderate greenhouse temperatures, in an average of sixty-five to seventy-five days.

DESCRIPTION OF THE DRAWING

My new variety of lily plant is illustrated by the accompanying photographic drawing, which shows the open bloom and buds in full color and particularly the distinctive deep pink, cream-centered flowers, copiously spotted in the center, and the upright flowering characteristics of the plant.

DESCRIPTION OF THE VARIETY

The following is a detailed description of my new variety of Asiatic hybrid lily with nomenclature according to The International Lily Register of The Royal Horticultural Society of London, England (Second Edition, 1969), and with color designations according to The R.H.S. Colour Chart published by the Society in 1966.

THE PLANT

Origin: Seedling.

Parentage:

*Seed parent.*—Lilium 'Peachblush'.

*Pollen parent.*—A pink flowered hybrid Lilium seedling selection from the cross of [('Enchantment'×an upright, pink Asiatic seedling)×-'Gypsy'].

Classification:

*Horticultural.*—Division I-A, Upright Asiatic Hybrid Lily, according to The Horticultural Classification of Lilies by The Royal Horticultural Society of London, England.

*Commercial.*—Asiatic Lily Cultivar.

Form: Single stem, erect and stately.

Height: About 90 to 125 cm. for stems produced by glasshouse forcing of bulbs having a circumference of about 15 to 18 cm. with adequate light levels.

Growth: Vigorous and upright.

Foliage:

*Quantity.*—Abundant.

*Leaf size.*—About 7 to 10 cm. long and about 0.5 to 1 cm. wide.

*Leaf shape.*—Lanceolate with acute apex.

*Texture.*—Leathery.

*Aspect.*—Glossy and lightly pubescent.

*Color.*—Dark green, somewhat lighter on the lower side.

Bulbs:

*Size.*—Various, depending upon age, ranging to about 25 cm. in circumference in commercial use.

*Color.*—White.

THE BUD

Form: Long ovoid with round base and obtuse apex.

Size: About 8 to 9 cm. long and about 5 cm. in circumference just prior to opening.

Opening rate: The bud opens slowly, taking about one hour in response to morning light.

Color: Soft pink with a flush of green along the midribs and at the tip just prior to opening and as the tepals begin to unfurl. The bud is lightly pubescent.

Peduncle:

*Length.*—About 4 to 6 cm., in average, but may become longer if light levels are too low or if the bulbs have been improperly stored prior to forcing.

*Color.*—Dark green.

THE FLOWER

Blooming habit: Once annually and profusely in midseason for Asiatic lilies.

Size: Medium, averaging about 13 to 15 cm. in diameter.

*Borne:* As a single, compact, racemose inflorescence, producing about 8 to 14 buds from a bulb having a circumference of about 12 to 16 cm. The stem produces secondary buds.

Shape: Cup-shaped upon first opening and becoming flattened as the tepals recurve by the second day.

Tepalage:

*Number.*—Six.

*Arrangement.*—Hexagonal.

*Shape.*—Outer tepals — Long elliptic with acute apex with an average width of about 2.5 cm. Inner tepals — Ovate with obtuse tip and averaging about 3 cm. wide.

Appearance.—Shiny.

Color.—The basic color is deep pink, 58B/C, with a cream-colored throat, 8B/C, which extends about 2 to 3 cm. from the base of the tepal, covering an area of about 2 to 3 cm. wide. Each tepal also has a softer pink flush, 58C, of about 1 to 2 mm. wide at the apex of the nectary furrows. The nectaries are very light cream to white and are pubescent.

*Tepal spotting.*—The tepals are copiously spotted with medium dark magenta spots in the cream-colored center of the flower and extending about 1 cm. into the pink portion of the petal body.

*Color changes.*—The flowers of this variety may lighten slightly to 58D at the tips as the flowers age. Strong heat and light can reduce the pink pigmentation, but there is little change of flower colors if the light and temperature levels are suitable for cut flower maintenance.

Pedicel:

*Length.*—About 4 to 8 cm., in average.

*Form.*—Sturdy and ascending to about 60° from the horizontal.

*Color.*—Dark green and slightly pubescent.

Persistence: The tepals stay on the stems for about three weeks.

Fragrance: None.

Disease resistance: The flower and plant are resistant to disease and in particular, they are resistant to Botrytis blight and Fusarium bulb rot.

Lasting quality: The flower is long lasting both on the plant and as a cut flower.

THE REPRODUCTIVE ORGANS

Stamens:

*Number.*—Six.

*Arrangement.*—Typical of genus Lilium.

*Pollen and dehisced anthers.*—Color: 183A to 180A.

Filaments.—Length: About 5 cm. Color: Soft cream, 18C, to pink, 36A.

Pistils:

*Number.*—One.

*Style.*—About 5 cm. long.

*Stigma.*—Medium in size and deep plum in color.

Character of ovary: Typical of genus Lilium.

THE FRUIT

Fertility: The fruit is fertile.

Shape: Ovoid.

Color at maturity: Soft brown, sometimes overlaid with soft plum.

My new variety of lily most closely resembles 'Peachblush' U.S. Plant Pat. No. 4,334 but is distinguished by having a pinker and less peach toned coloration, a lighter toned cream center and much more conspicuous spotting. The new plant is also much taller and with shorter leaves than 'Peachblush'.

I claim:

1. A new and distinctive variety of Asiatic hybrid lily plant, substantially as herein shown and described, characterized in particular by its attractively spotted, cream throated, deep pink flowers and the excellence of its flower form; by its relatively long stemmed, short leaved, upright flowering silhouette; and its versatility both as a garden plant and as a cut flower variety well suited for forcing into flower out of season.

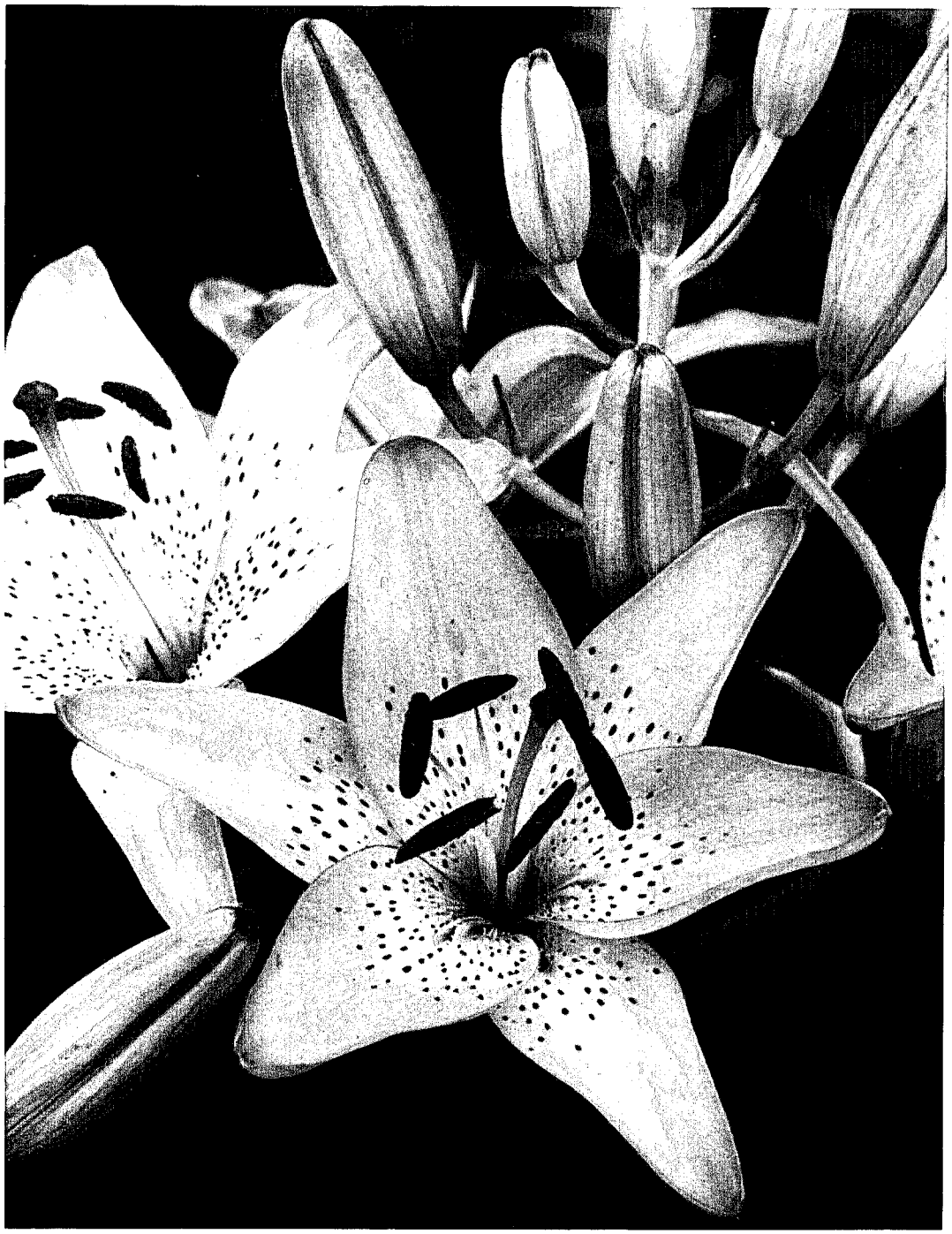

* * * * *